United States Patent [19]

Garay et al.

[11] Patent Number: 4,861,268

[45] Date of Patent: Aug. 29, 1989

[54] TOOTH-ANCHORED BENEFICIAL AGENT DELIVERY DEVICE

[75] Inventors: Gabriel L. Garay, Atherton; Anne-Ly Garay, Redwood City; Robert Tacy, Los Altos Hills, all of Calif.

[73] Assignee: Transpharm Group, San Francisco, Calif.

[21] Appl. No.: 206,098

[22] Filed: Jun. 13, 1988

[51] Int. Cl.⁴ .............................................. A61C 19/06
[52] U.S. Cl. ..................................... 433/229; 433/23; 433/80; 424/435
[58] Field of Search .................. 433/229, 9, 23, 80, 433/215; 424/435; 604/77

[56] References Cited

U.S. PATENT DOCUMENTS

| | | | |
|---|---|---|---|
| 307,537 | 11/1884 | Foulks | 424/435 |
| 2,378,279 | 6/1945 | Begg | 433/23 |
| 2,625,158 | 1/1953 | Lee et al. | 604/93 |
| 2,773,502 | 12/1956 | Kaslow et al. | 604/57 |
| 2,835,628 | 5/1958 | Saffir | 433/229 |
| 3,386,440 | 6/1968 | Cohen | 604/77 |
| 3,429,308 | 2/1969 | Russell | 424/435 |
| 3,503,127 | 3/1970 | Kasdin et al. | 433/199.1 |
| 3,600,807 | 8/1971 | Sipos | 433/167 |
| 3,754,332 | 8/1973 | Warren | 433/217.1 |
| 3,786,813 | 1/1974 | Michaels | 604/892.1 |
| 3,788,322 | 1/1974 | Michaels | 604/890.1 |
| 3,797,492 | 3/1974 | Place | 604/890.1 |
| 3,901,232 | 8/1975 | Michaels et al. | 604/892.1 |
| 3,911,009 | 10/1975 | DeFoney et al. | 424/435 |
| 3,944,064 | 3/1976 | Bashaw et al. | 424/422 |
| 4,020,558 | 5/1977 | Cournut et al. | 433/80 |
| 4,039,653 | 8/1977 | DeFoney et al. | 424/435 |
| 4,055,178 | 10/1977 | Harrigan | 604/890.1 |
| 4,175,326 | 11/1979 | Goodson | 433/80 |
| 4,312,347 | 1/1982 | Magoon et al. | 604/891.1 |
| 4,313,438 | 2/1982 | Greatbatch | 604/20 |
| 4,314,554 | 2/1982 | Greatbatch | 604/20 |
| 4,485,805 | 12/1984 | Foster, Jr. | 128/898 |
| 4,681,544 | 7/1987 | Anthony | 433/229 |
| 4,685,883 | 8/1987 | Jernberg | 433/215 |
| 4,741,700 | 5/1988 | Barabe | 433/229 |

*Primary Examiner*—John J. Wilson
*Attorney, Agent, or Firm*—Irell & Manella

[57] ABSTRACT

A tooth-anchored beneficial agent delivery device comprising an anchor-member that is semipermanently attached to a tooth, such as by an adhesive, bonding or a tooth-encircling band, and one or more agent-carrying cartridges that are removably connected to the anchor member such as by a ball-and-socket mechanism.

10 Claims, 2 Drawing Sheets

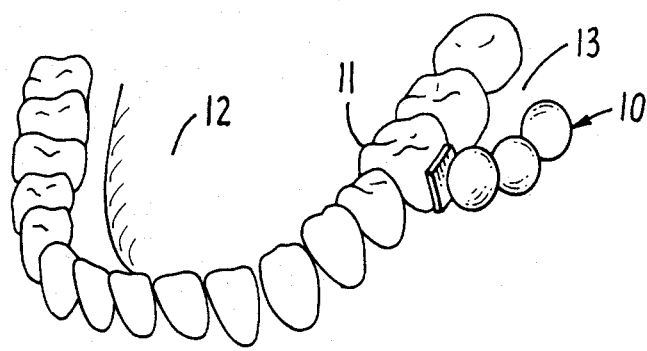
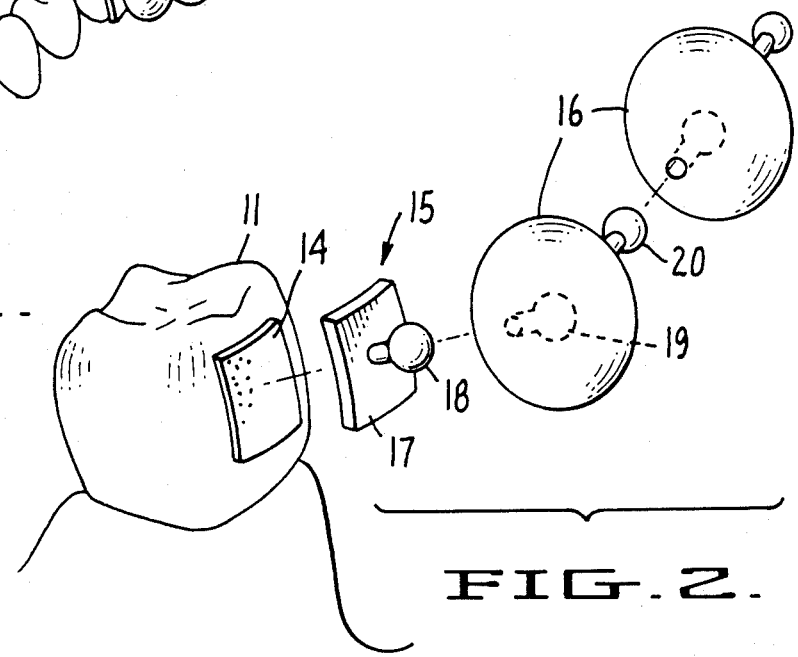
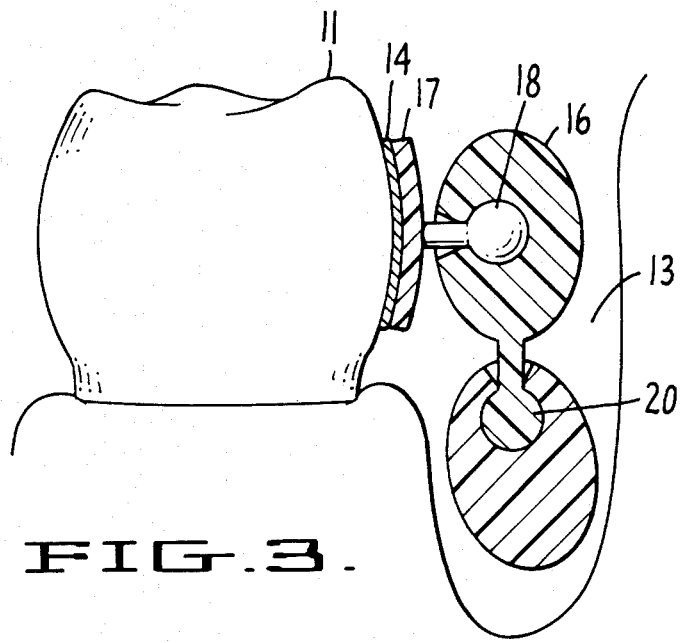
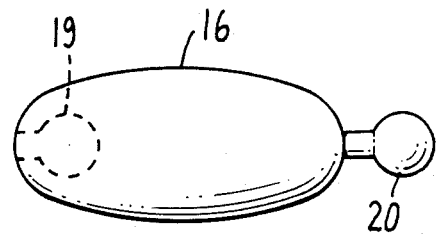
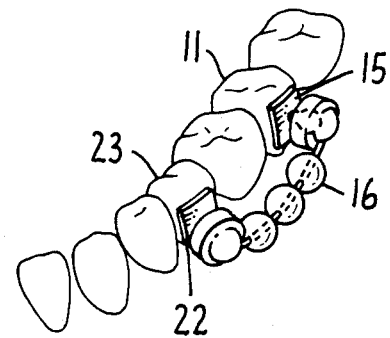

TOOTH-ANCHORED BENEFICIAL AGENT DELIVERY DEVICE

DESCRIPTION

1. Technical Field

The invention is in the field of drug delivery. More specifically it is in the field of sustained release devices for administering drugs or other beneficial agents orally.

2. Background

The prolonged delivery of drugs orally has been a major challenge and a long desired objective in drug therapy. This is a favored route for drug administration. It is estimated that 65% of all drugs are ingested. The successful accomplishment of prolonged oral drug delivery has great therapeutic significance in the treatment of various diseases and conditions.

Systemic and transdermal sustained drug delivery systems have been developed which are capable of delivering constant amounts of therapeutic substances from several days to several months. The major limitation to long-term oral delivery, however, is the 8-16 hour gastrointestinal transit time of an ingested substance. In order to achieve uninterrupted action for longer than 24 hours by a therapeutic substance, its passage needs to be slowed in the gastrointestinal tract or the delivery device supplying the drug has to be fixed or immobilized within the tract.

Attempts have been made either to incorporate drugs into floating devices which would empty less readily from the stomach (N. Eng. J. Med. (1981) 304:1365-1366) or to utilize insoluble bioadhesive polymers as carriers for drugs. It is thought that a delivery device made of such a polymer would adhere to the mucosa of the gastrointestinal tract and be able to discharge its contents in a sustained manner ("Advances in Drug Delivery Systems" J. M. Anderson and S. W. Kim, Eds, Elsevier, Amsterdam Vol 1, 1986, pp. 47-57). Although some of these approaches have had limited success in animals, they have proved to be impractical in humans thus far.

The diseases and conditions of dentition and of the oral cavity, on the other hand, have been more freely targeted for timed-release chemicals or therapeutic substances which have been placed inside delivery devices intended to act for longer than 24 hours. Considerable attention has been paid to the control of bad breath or taste in the mouth by means of dispensing deodorizers or chemicals that impart a pleasant taste or mask unpleasant odors. U.S. Pat. Nos. 3,503,127 and 3,600,807 describe inventions where a cup or pocket is formed in a denture or in an artificial tooth in order to store and make available breath- and taste-refreshing chemicals. U.S. Pat. No. 2,835,628 proposes the use of medicated tape impregnated with prolonged-released sodium fluoride. This device is made to adhere to the tooth's surface for the prevention of dental caries. In another invention a soluble tape impregnated with fluoride or other chemicals for the local treatment of oral diseases is inserted between teeth and left there to dissolve and disperse its active ingredient (U.S. Pat. No. 3,754,332).

Other inventions propose to employ biocompatible adhesives and patches in order to affix tablets directly to the buccal mucosa for odor masking, for buccal delivery of local anesthetics and antihistamines, or even for the local release of nitroglycerin (U.S. Pat. Nos. 3,911,099 and 4,039,653). However, most of these delivery systems are expected to remain fixed only for a relatively short period of time.

French Pat. No. 2,278,317 describes a medicated tab attached to a blunt-nosed spike which can be pushed into the space between two adjacent teeth. The objective is to provide a local, sustained release of medications when the tab comes into contact with the gum line.

The use of a medicated pad placed over the open socket of a freshly extracted tooth for the relief of pain and hemorrhage was also suggested (U.S. Pat. No. 3,386,440). There is significant interest in treating gingivitis and periodontal diseases by placing long-acting medications locally in the vicinity of the inflamed gum or by introducing active substances directly into the disease-induced subgingival pockets (J. Periodontology (1984) 11:651-651).

Goodson (U.S. Pat. No. 4,175,326) discloses capillary hollow fibers filled with the antibiotic tetracycline. These hollow fiber bands are slipped over each tooth, then rolled down into the periodontal pocket in order to achieve a high local concentration of the antibiotic. The control of the local microbial flora linked to the pathogenesis of this disease is the aim of this process.

The further utilization of drug-loaded hollow fiber bands for the therapy of other oral conditions requiring the local availability of anti-inflammatory, antifungal, or immune modulator substances is also suggested. Jernberg in U.S. Pat. No. 4,685,883 describes a delivery system of biodegradable, time-release microspheres encapsulating drugs and packed tightly into the subgingival periodontal pocket. He also suggests the use of a biodegradable matrix adhesively attached to the root of the tooth for the more effective local treatment of the periodontal disease is also suggested.

U.S. Pat. No. 4,681,544 describes an oral pack retention system to hold surgical dressings over a fresh wound site in order to prevent infection and hemorrhage after oral or periodontal surgery. The pack may be impregnated with drugs such as antibiotics or analgesics. The patent extends the invention of Goodson and suggests that its system, using wires and adhesives, could retain a medicated pack at the root of a tooth for the local treatment of periodontal disease. A complex and extensive system of individually adjustable splints and wires to support the pack is described.

Since most of these oral, active-substance delivery systems target the local therapy of oral diseases, they have significant limitations as to the amount of drug which can be placed, as well as limitations in the amount of time the devices will remain in place. Furthermore, there can be difficulties when these devices need to be removed, once their active content has been discharged. Replacement for repeated administration has been particularly ignored.

The prior art is particularly devoid of devices which are designed for the sustained delivery of drugs and/or other beneficial substances for the whole body, rather than just the oral cavity. There is a need for devices which can be repeatedly replenished with active substances, are easily tolerated in the mouth, and do not interfere with speech, food mastication or oral hygiene. The present invention provides such devices.

DISCLOSURE OF THE INVENTION

The invention is a beneficial agent delivery device adapted to be semipermanently affixed to a tooth comprising:
- (a) an anchor member that is adapted to be affixed to the side of a tooth out of the way of the biting surface of the teeth;
- (b) a cartridge member adapted to be removably affixed to said anchor member, said cartridge member containing a beneficial agent and being capable of releasing said agent to the oral cavity.

The invention thus provides a tooth-borne platform that may be worn comfortably and from which drugs or other beneficial agents may be released into the oral cavity and gastrointestinal tract at predetermined doses and dosage regimens. The agent-carrying means of the device may be divided into a multiplicity of individual cartridges thus facilitating tailoring the dose, and/or dosage regimen or the administration of a multiplicity of agents simultaneously or in a predetermined sequence. Further, since the agent-carrying means are removable, they may be easily removed and, if necessary, replaced immediately or after a predetermined interval. Since the device permits sustained release it facilitates patient compliance.

Further the mounting of the invention device is a nonsurgical, painless event. The device, when properly worn, should not inhibit normal physiological functions or cause significant irritation to oral tissues.

BRIEF DESCRIPTION OF THE DRAWINGS

In the drawings, which are not to scale and in which like parts are referred to by the same reference numeral:

FIG. 1 is a view of a lower dentition showing an embodiment of the invention device anchored to a tooth.

FIG. 2 is an enlarged exploded view of the device of FIG. 1.

FIG. 3 is a cross-sectional view of the device of FIG. 1.

FIG. 4 is a plan view of one of the removable elements of the device of FIG. 1.

FIG. 5 depicts another embodiment of the invention device.

DETAILED DESCRIPTION OF EMBODIMENTS SHOWN IN DRAWINGS

Figure 6:
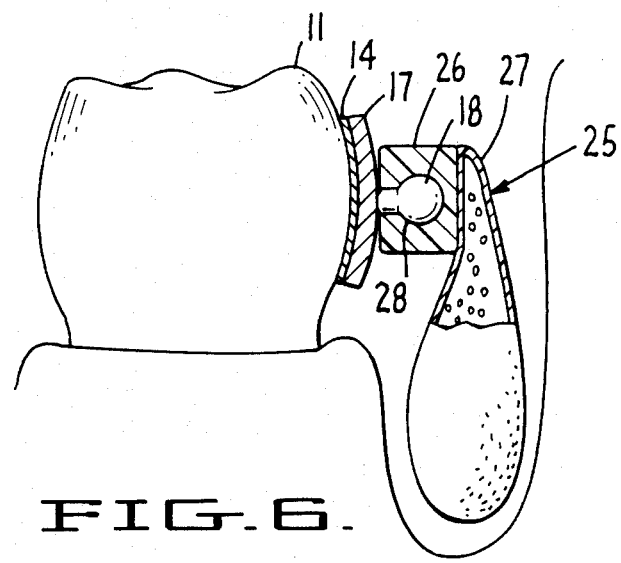
FIG. 6 is a sectional view of still another embodiment of the invention device.

"Beneficial agents" as used herein is intended to include drugs, vitamins, breath deodorizers, and other chemicals or compositions that are administered orally to humans or animals to achieve a beneficial effect on the recipient. The term "drug" as used herein broadly includes physiologically and/or pharmacologically active substances for producing a local effect within the mouth or gastrointestinal tract or a systemic effect at a remote site within the body.

FIGS. 1–4 and 9 depict one embodiment of the invention device, generally designated 10, anchored to a tooth 11 and show the position of the device relative to the tongue 12 and cheek vestibule 13. As shown, in FIGS. 1 and 9 device 10 lies buccally within the vestibule of the cheek/lips out of the way of the biting surface of the teeth. While the device is shown in a buccal position, it could, if desired, be positioned on the lingual side of the teeth. Further, the device may be mounted in either the upper or lower dentition.

Referring to FIG. 2, the device includes an adhesive layer 14 one face of which is adhered to the labial or buccal (outer) side of the tooth, an anchor member 15, and a multiplicity of cartridges 16. The anchor member 15 is semipermanently affixed (i.e., for at least a day and usually for at least a week) to the labial side of the tooth via the adhesive layer and consists of a flat base 17 and a ball member 18 that extends outwardly from the flat base. The adhesive may be biodegradable or nondegradable, but in any event should be such as to permit the anchor member to be removed from the tooth when the delivery is no longer desired. Means other than adhesives such as bonding or mechanical devices may be used to affix the anchor member to the tooth. The cartridge capsule that is attached directly to the anchor member has a socket 19 formed in its surface that is adapted to receive ball member 18. Alternatively, other equivalent connecting means for removably connecting the cartridge to the anchor may be used. The cartridge may thus be removably connected to the anchor member by the ball-and-socket combination. Ball-and-socket connection permits rotational movement of the cartridge about the ball-socket axis. When it is desired to have a multiplicity of individual cartridges connected in chain-fashion to the anchor member the initial cartridge in the chain carries a ball member 20 on its exterior surface. That ball member is received in a socket formed in the second cartridge in the chain, and so forth. As shown the ball member and socket in the intermediate cartridges in the chain are positioned along the same axis. Alternatively, a branched assembly is possible by providing the cartridges with more than one interconnection site. Accordingly, the cartridges are connected to the anchor in a manner that permits each cartridge to rotate, thereby imparting the chain with the ability to conform to the anatomy of the cheek/lip vestibule. Further, the chain is able to flex freely to avoid interfering with chewing or dental hygiene.

At least one of the cartridges, and preferably all of the cartridges contains beneficial agent. By using a multiplicity of unit dosage cartridges, doses may be easily adjusted via the number of cartridges included in the chain. A cartridge may contain more than one agent or when more than one cartridge is employed the individual cartridges may contain different agents. The structure of the cartridge and/or the formulation of the agent within the cartridge are preferably such that the release of agent from the cartridge will be over a sustained time period. It will be appreciated that the agent may be formulated in such a manner (e.g., in coated microcapsules) that while the formulation may be released initially in the oral cavity that the release of agent from the formulation occurs elsewhere in the gastrointestinal tract. Various mechanisms to achieve sustained release such as diffusion, osmosis, bioerosion, swelling, and dissolution may be employed. The cartridge may be of monolithic or container construction. Monolithic structures are composed entirely of drug formulation or drug dispersed in a matrix material. Container structures comprise a housing or wall that defines a lumen and an agent formulation within the lumen. In either structure, the cartridge is made of a material that permits the formation of the socket/ball member or other interconnecting means required to interconnect the cartridges. In container structures, depending on the nature of the agent release mechanism, the wall may also be required to be permeable to the agent or be semipermeable to permit aqueous fluids to be imbibed into the cartridge to effect agent release by an osmotic mechanism. Alternatively, the cartridge may be porous so as to permit saliva to enter the cartridges to contact the agent or agent-release mechanism within the cartridge. The agent within the cartridge may be neat or formulated with carriers or diluents, again depending upon the nature of the agent-release mechanism.

The shape of the cartridges 16 is generally not critical and will normally be chosen for ease of manufacture and comfortable residence within the cheek/lip vestibule. Shapes that are typically used for tablets, capsules, and pills are acceptable.

FIG. 5 shows a variation of the device of FIG. 1 in which a second anchor member 22 is attached to the outer site of another tooth 23 in the lower dentition and the cartridge at the end of the chain is removably connected to the second anchor member. The chain of cartridges is thus suspended between the two anchor members along the lower dentition. Such assembly assures that the chain is kept out of the way of the biting surfaces and is maintained in an extended configuration.

FIG. 6 depicts another embodiment of the invention in which the cartridge, generally designated 25, is composed of a rigid base 26 to which is affixed a flexible bag 27 that contains the agent. The base has a socket 28 to permit the cartridge to be removably affixed to the anchor member on the tooth. Again, depending upon the mechanism of agent delivery, the bag wall may be agent-permeable, semipermeable, or porous. Such embodiments, because of the pliancy, softness, and flexibility of the bag, may be more comfortable to some wearers.

Figure 7:
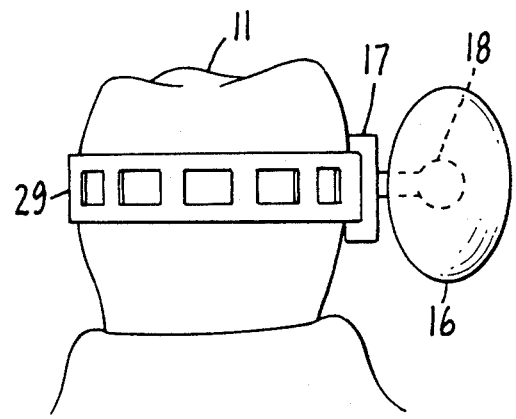
FIG. 7 is a cross-sectional view of yet another embodiment of the invention device.
Figure 8:
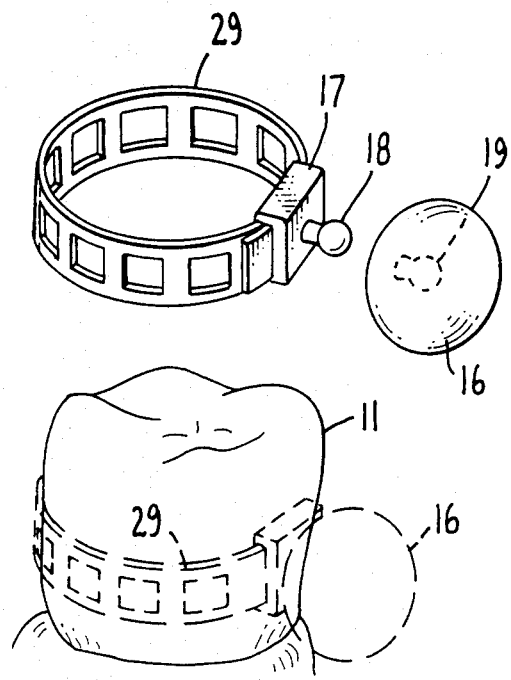
FIG. 8 is an exploded view of the device of FIG. 7.
Figure 9:
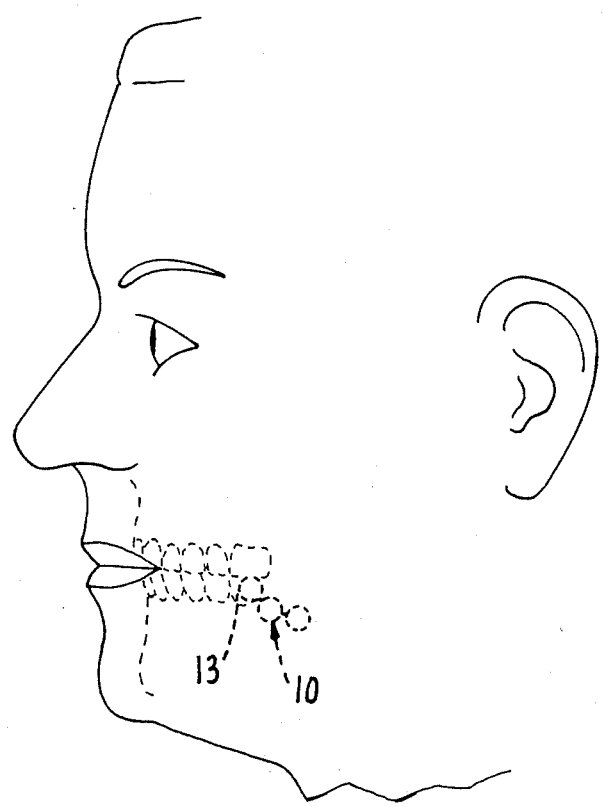
FIG. 9 is a partial view of a human head showing the device of FIG. 1 anchored to a tooth and the anatomical position of the device.

FIGS. 7 and 8 depict a variation of the device of FIG. 1 in which a tooth-encircling band or "lasso" 29 is used instead of or in combination with an adhesive as a means for attaching the anchor member to a tooth. The band may be made of an elastic material, a rigid material, or may be mechanically adjustable (e.g., by a ratchet mechanism) so that its girth may be altered to encircle the tooth snugly. With elastic materials the band is self-adjusting to encircle the tooth snugly. In the case of rigid materials, the girth of the band is preset to provide a snug fit. The band may be further secured with an adhesive or cement. While the band is shown encircling a single tooth, it may encircle more than one tooth if desired.

Other embodiments of the invention that are obvious to those of skill in the fields of drug delivery devices, orthodontics, or related fields are intended to be within the scope of the following claims.

We claim:

1. A beneficial agent delivery device adapted to be semipermanently affixed to a tooth comprising:
    (a) an anchor member that is adapted to be removably affixed to the side of a tooth out of the way of the biting surface of the teeth; and
    (b) a cartridge member adapted to be removably affixed to said anchor member, said cartridge member containing a beneficial agent, being capable of releasing said agent into the oral cavity, and comprising a chain of individual cartridges that are linked to each other.

2. The device of claim 1 including
    (c) means for semipermanently affixing said anchor member to the tooth.

3. The device of claim 2 wherein said means is an adhesive or a bonding agent.

4. The device of claim 2 wherein the means is a band that encircles the tooth and to which the anchor member is attached.

5. The device of claim 4 wherein the girth of the band is adjustable.

6. The device of claim 4 wherein the girth of the band is preset to encircle the tooth snugly.

7. The device of claim 1 wherein the anchor member comprises a base member that is adapted to be affixed to the side of the tooth and a ball member extending outwardly from the base member and the cartridge member has a socket into which the ball member fits.

8. The device of claim 1 wherein said chain of individual cartridges are linked to each other in a ball-and-socket means.

9. The device of claim 1 including
    (c) a second anchor member that is adapted to be affixed to the same side of another tooth out of the way of the biting surface of the teeth and wherein one end of said chain is removably affixed to the anchor member and the other end of the chain is removably affixed to the second anchor member.

10. A beneficial agent delivery device adapted to be semipermanently affixed to a tooth comprising:
    (a) an anchor member that is adapted to be affixed to the side of a tooth out of the way of the biting surface of the teeth; and
    (b) a cartridge member comprising a base member that is removably affixed to the anchor member and a flexible bag attached to the base member whose lumen contains a beneficial agent and from which the beneficial agent is released into the oral cavity.

* * * * *